(12) United States Patent
Takenaka et al.

(10) Patent No.: US 8,852,954 B2
(45) Date of Patent: Oct. 7, 2014

(54) NUCLEIC ACID MOLECULE HAVING BINDING AFFINITY TO RODENT-DERIVED IGG ANTIBODY, BINDER, DETECTION REAGENT, AND DETECTION KIT

(75) Inventors: Hiromi Takenaka, Tokyo (JP); Yoshihito Yoshida, Tokyo (JP); Katsunori Horii, Tokyo (JP); Makio Furuichi, Tokyo (JP); Hirotaka Yagi, Tokyo (JP); Jou Akitomi, Tokyo (JP); Mineko Yamaguchi, Tokyo (JP); Shintarou Katou, Tokyo (JP); Kensaku Nishikata, Tokyo (JP); Iwao Waga, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 88 days.

(21) Appl. No.: 13/511,618

(22) PCT Filed: Aug. 21, 2009

(86) PCT No.: PCT/JP2009/064682
§ 371 (c)(1),
(2), (4) Date: Sep. 27, 2012

(87) PCT Pub. No.: WO2011/021308
PCT Pub. Date: Feb. 24, 2011

(65) Prior Publication Data
US 2013/0022967 A1    Jan. 24, 2013

(51) Int. Cl.
*G01N 33/567*    (2006.01)
*C12Q 1/68*    (2006.01)
*C07H 21/02*    (2006.01)
*G01N 33/53*    (2006.01)
*C12N 15/115*    (2010.01)

(52) U.S. Cl.
CPC .......... *C12N 15/115* (2013.01); *G01N 33/5308* (2013.01); *C12N 2310/16* (2013.01)
USPC ............................ 436/501; 435/6.1; 536/23.1

(58) Field of Classification Search
USPC ............................ 436/501; 435/6.1; 536/23.1
See application file for complete search history.

(56) References Cited

FOREIGN PATENT DOCUMENTS

| CN | 101275137 A | 10/2008 |
| JP | 2009-46494 A | 3/2009 |

OTHER PUBLICATIONS

Yoshida et al., "Quantitative and Sensitive Protein Detection Strategies Based on Aptamers", Proteomics—Clinical Applications, vol. 6, No. 11-12, Dec. 8, 2012, pp. 574-580.

(Continued)

*Primary Examiner* — Jon E Angell
(74) *Attorney, Agent, or Firm* — Sughrue Mion, PLLC

(57) ABSTRACT

The invention provides a nucleic acid molecule having a binding affinity to a rodent-derived IgG antibody, which can be prepared easier than an antibody and has a binding affinity equivalent or superior to that of an antibody, a binder using the nucleic acid molecule, a detection reagent, and a detection kit. The nucleic acid molecule of the invention has a binding affinity to a rodent-derived IgG antibody and has a dissociation constant of 1 μM or less. The binder for a rodent-derived IgG antibody of the present invention includes the nucleic acid molecule of the present invention. The detection reagent for detecting a rodent-derived IgG antibody of the invention includes the binder for a rodent-derived IgG antibody of the invention. The detection kit for detecting a rodent-derived IgG antibody of the invention includes the detection reagent for detecting a rodent-derived IgG antibody of the invention.

14 Claims, 11 Drawing Sheets

(56) References Cited

OTHER PUBLICATIONS

Liao et al., "Aptamer-Based Sensitive Detection of Target Molecules via RT-PCR Signal Amplification", Bioconjugate Chemistry, vol. 21, No. 12, Dec. 15, 2010, pp. 2183-2189.

Ma et al., "Target Replacement Strategy for Selection of DNA Aptamers Against the Fc Region of Mouse IgG", Genetics and Molecular Research, vol. 12, No. 2, Jan. 1, 2013, pp. 1399-1410.

Extended European Search Report dated Jul. 3, 2013 issued by the European Patent Office in counterpart European Application No. 09848504.8.

Yoshida et al., "Rabbit antibody detection with RNA aptamers", Analytical Biochemisry, 2008, pp. 217-222, vol. 375.

Abramoff et al., "Image Processing with ImageJ", Biophotonics International, 2004, pp. 36-42, vol. 11, No. 7.

Sakai et al., "RNA aptamers specifically interact with the Fc region of mouse immunoglobulin G", Nucleic Acids Symposium Series, 2008, pp. 487-488, No. 52.

Office Action dated Jun. 14, 2013 issued by the Australian Patent Office in counterpart Australian Application No. 2009351455.

Faaber et al., "Cross-reactivity of Human and Murine Anti-DNA Antibodies with Heparan Sulfate", J. Clin. Invest., vol. 77, Jun. 1986, pp. 1824-1830.

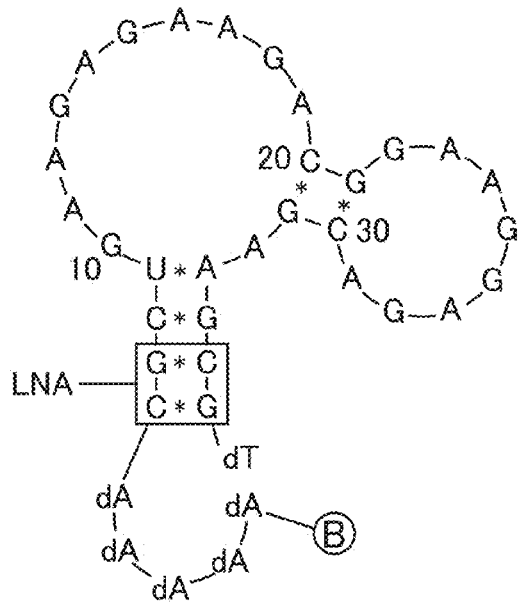
MIG-m034
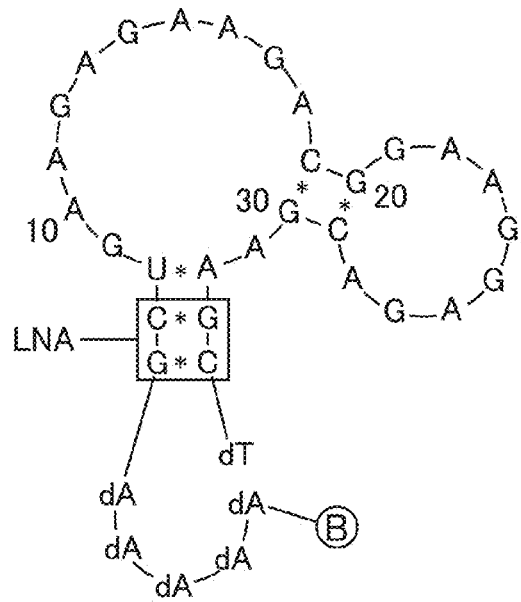
MIG-m035
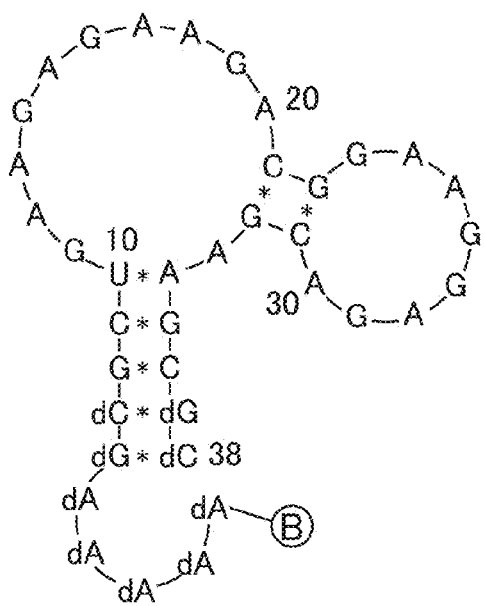
MIG-m036
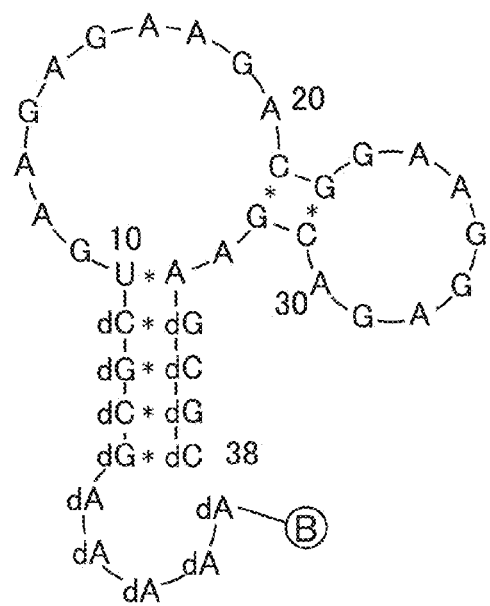
MIG-m037
FIG. 2

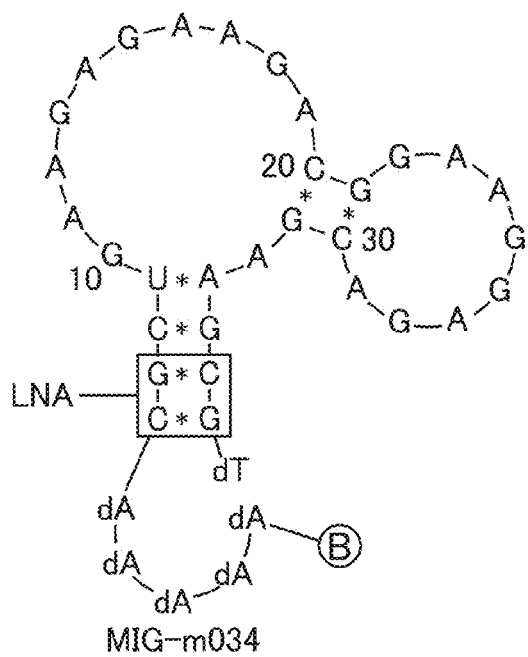
MIG-m034
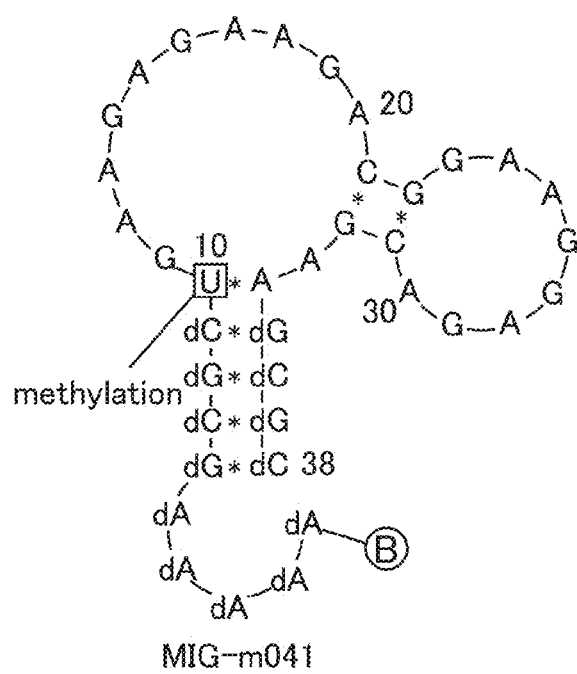
MIG-m041
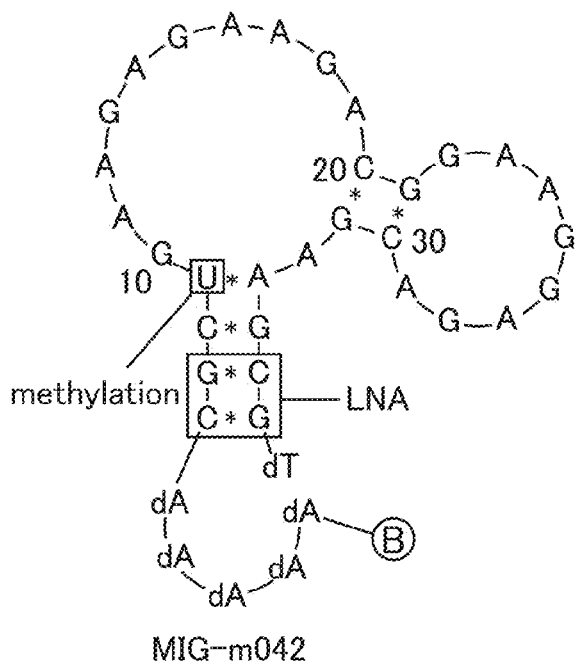
MIG-m042
FIG. 3

NUCLEIC ACID MOLECULE HAVING BINDING AFFINITY TO RODENT-DERIVED IGG ANTIBODY, BINDER, DETECTION REAGENT, AND DETECTION KIT

CROSS REFERENCE TO RELATED APPLICATIONS

This application is a National Stage of International Application No. PCT/JP2009/064682 filed Aug. 21, 2009, the contents of which is incorporated herein by reference in its entirety.

TECHNICAL FIELD

The present invention relates to a nucleic acid molecule having a binding affinity to a rodent-derived IgG antibody, a binder, a detection reagent, and a detection kit.

BACKGROUND ART

Since the antigen-antibody reaction is a highly-specific reaction, it is applied to the detection or the like of specific proteins and the like. For example, ELISA is a method of detecting antigens (proteins and the like) as follows. That is, an antibody labeled with an enzyme is allowed to react with a specific antigen (protein or the like) in a sample to form a complex, the complex is captured by an antigen immobilized to a bead or the like, and a chromogenic substrate is allowed to act on the enzyme. Further, antibodies are used as medicines utilizing their specificity (for example, see Patent Document 1).

As detection reagents, antibodies derived from rodents such as mice and rats are used. In a detection kit using a rodent-derived antibody, an antigen that specifically binds to a rodent-derived antibody is used. However, there are problems that the production of antibodies is difficult and the handling of antibodies is complicated.

RELATED ART DOCUMENT

Patent Document

[Patent Document 1] JP 2009-46494 A

DISCLOSURE OF THE INVENTION

Problem to be Solved by the Invention

The present invention is intended to provide a nucleic acid molecule having a binding affinity to a rodent-derived IgG antibody, which can be easily produced and handled and has a binding affinity equivalent or superior to that of an antibody.

Means for Solving Problem

The nucleic acid molecule of the present invention has a specific binding affinity to a rodent-derived IgG antibody and has a dissociation constant of 1 μM or less. Here, the concentration unit M is equal to 1 mol/dm³ or 1 mol/L.

The binder for a rodent-derived IgG antibody of the present invention includes the nucleic acid molecule of the present invention.

The detection reagent for detecting a rodent-derived IgG antibody of the present invention includes the binder for a rodent-derived IgG antibody of the present invention.

The detection kit for detecting a rodent-derived IgG antibody of the present invention includes the detection reagent for detecting a rodent-derived IgG antibody of the present invention.

Effects of the Invention

The nucleic acid molecule of the present invention can bind to a rodent-derived IgG antibody with high specificity. Further, the nucleic acid molecule of the present invention can be easily produced and handled as compared to an antibody.

BRIEF DESCRIPTION OF DRAWINGS

FIG. 2 is a schematic view showing the predicted secondary structures of aptamers.

FIG. 3 is a schematic view showing the predicted secondary structures of aptamers.

Figure 1:
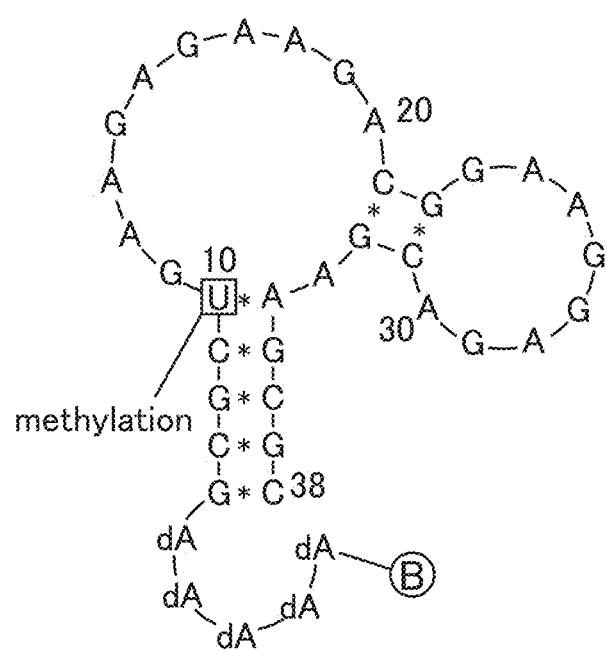
FIG. 1 is a schematic view showing the predicted secondary structure of an aptamer.

DESCRIPTION OF EMBODIMENTS (Nucleic Acid Molecule of Present Invention)

As described above, the nucleic acid molecule of the present invention has a specific binding affinity to a rodent-derived IgG antibody and has a dissociation constant of 1 μM or less. The dissociation constant is preferably 200 nM or less, more preferably 100 nM or less, and still more preferably 10 nM or less. In the present invention, rodents refer to Mammalia: Rodentia. Examples of rodents include mice and rats. The nucleic acid molecule of the present invention is preferably a nucleic acid molecule that specifically binds to mouse-derived IgG at the aforementioned dissociation constant. Likewise, the nucleic acid molecule of the present invention is preferably a nucleic acid molecule that specifically binds to rat-derived IgG at the aforementioned dissociation constant.

The nucleic acid molecule of the present invention may be a single-stranded nucleic acid or a double-stranded nucleic acid, for example. Examples of the single-stranded nucleic acid include single-stranded RNA and single-stranded DNA; and examples of the double-stranded nucleic acid include double-stranded RNA and double-stranded DNA. In the case where the nucleic acid molecule of the present invention is the double-stranded nucleic acid, for example, the nucleic acid molecule may be dissociated into single-stranded nucleic acids by denaturation or the like prior to use.

The nucleic acid molecule of the present invention may be, for example, an RNA molecule or a DNA molecule, and is preferably an RNA molecule. Further, the nucleic acid molecule of the present invention may be, for example, DNA or RNA as described above, and nucleotide residues that form the nucleic acid molecule may contain both deoxyribonucleotide, which is a building block of DNA, and ribonucleotide, which is a building block of RNA. Further, examples of the nucleic acid molecule of the present invention include ssDNA, ssRNA, dsDNA, and dsRNA; and there are no limitations on the number of strands and whether or not the nucleic acid is modified.

In the nucleic acid molecule of the present invention, a base in the nucleotide may be a natural base (non-artificial base) such as adenine (a), cytosine (c), guanine (g), thymine (t), or uracil (u) or an artificial base such as a modified base or an altered base that has functions similar to those of the natural base (a, c, g, t, or u). Examples of the artificial base that has functions similar to those of the natural base include an artificial base that is bindable to cytosine (c) in place of guanine (g), an artificial base that is bindable to guanine (g) in place of cytosine (c), an artificial base that is bindable to thymine (t) or uracil (u) in place of adenine (a), an artificial base that is bindable to adenine (a) in place of thymine (t), and an artificial base that is bindable to adenine (a) in place of uracil (u). Examples of the modified base include a methylated base, 2'-fluorouracil, 2'-aminouracil, 2'-O-methyl uracil, and 2-thiouracil. Further, for example, the nucleic acid molecule of the present invention may include a peptide nucleic acid such as PNA; a Locked Nucleic Acid (LNA); and a 2'-O,4'-C-Ethylenebridged Nucleic Acid (ENA).

The nucleic acid molecule of the present invention may be, for example, a single-stranded nucleic acid and represented by the following general formula (I).

[Formula 1]

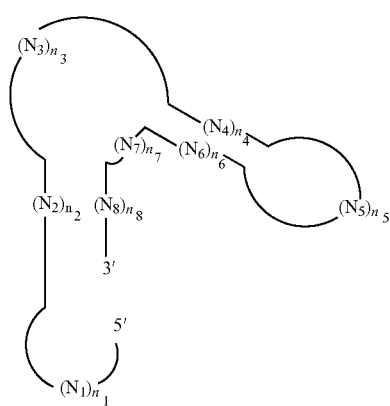

(I)

In the formula (I), each of $N_1$, $N_2$, $N_3$, $N_4$, $N_5$, $N_6$, $N_7$, and $N_8$ indicates a nucleotide residue;

$n_1$, $n_2$, $n_3$, $n_4$, $n_5$, $n_6$, $n_7$, and $n_8$ respectively indicate the numbers of the nucleotide residues $N_1$, $N_2$, $N_3$, $N_4$, $N_5$, $N_6$, $N_7$, and $N_8$;

each of $N_1$, $N_3$, $N_5$, and $N_7$ is capable of forming a loop structure;

$N_2$ and $N_8$ are capable of forming a stem structure by binding to each other through hydrogen bonding; and $N_4$ and $N_6$ are capable of forming a stem structure by binding to each other through hydrogen bonding.

In the present invention, the phrase "capable of forming a loop structure" encompasses, for example, a state where a loop structure actually is formed and a state where a loop structure can be formed depending on conditions even if it is not yet formed. Further, the state where something is "capable of forming a loop structure" encompasses, for example, the case where it is confirmed through an experiment and the case where it is predicted through simulation with a computer or the like. Similarly, in the present invention, the phrase "capable of forming a stem structure" encompasses, for example, a state where a stem structure actually is formed and a state where a stem structure can be formed depending on conditions even if it is not yet formed. Further, the state where something is "capable of forming a stem structure" encompasses, for example, the case where it is confirmed through an experiment and the case where it is predicted through simulation with a computer or the like.

In the formula (I), there is no particular limitation on the number of nucleotide residues in the whole single-stranded nucleic acid, and the number of nucleotide residues is, for example, in the range from 7 to 150, preferably in the range from 10 to 100, and more preferably in the range from 15 to 60.

There is no particular limitation on the number of nucleotide residues $n_1$ in $N_1$, and the number of nucleotide residues $n_1$ is, for example, in the range from 0 to 40, preferably 1 to 25, and more preferably 4 to 10.

There is no particular limitation on the number of nucleotide residues $n_2$ in $N_2$, and the number of nucleotide residues $n_2$ is, for example, in the range from 1 to 40, preferably 2 to 20, and more preferably 2 to 8.

There is no particular limitation on the number of nucleotide residues $n_3$ in $N_3$, and the number of nucleotide residues $n_3$ is, for example, in the range from 1 to 50, preferably 1 to 30, and more preferably 1 to 15.

There is no particular limitation on the number of nucleotide residues $n_4$ in $N_4$, and the number of nucleotide residues $n_4$ is, for example, in the range from 1 to 40, preferably 1 to 20, and more preferably 1 to 10.

There is no particular limitation on the number of nucleotide residues $n_5$ in $N_5$, and the number of nucleotide residues $n_5$ is, for example, in the range from 1 to 50, preferably 1 to 30, and more preferably 1 to 15.

There is no particular limitation on the number of nucleotide residues $n_6$ in $N_6$, and the number of nucleotide residues $n_6$ is, for example, in the range from 1 to 40, preferably 1 to 20, and more preferably 1 to 10.

There is no particular limitation on the number of nucleotide residues $n_7$ in $N_7$, and the number of nucleotide residues $n_7$ is, for example, in the range from 1 to 50, preferably 1 to 30, and more preferably 1 to 10.

There is no particular limitation on the number of nucleotide residues $n_8$ in $N_8$, and the number of nucleotide residues $n_8$ is, for example, in the range from 1 to 40, preferably 2 to 20, and more preferably 2 to 8.

Although there are no particular limitations on the numbers of nucleotide residues $n_1$, $n_2$, $n_3$, $n_4$, $n_5$, $n_6$, $n_7$, and $n_8$, the numbers of nucleotide residues preferably satisfy the following equality and inequality.

$$n_2 = n_8, n_4 = n_6, (n_3 + n_7) > n_5$$

The nucleic acid molecule represented by the formula (I) may be a DNA molecule or an RNA molecule, and is preferably an RNA molecule. In the case where the nucleic acid molecule of the present invention is an RNA molecule, the nucleic acid molecule is preferably a ribonuclease-resistant nucleic acid molecule. There is no particular limitation on the method of allowing the nucleic acid molecule to be ribonuclease-resistant, and examples of the method include a method of modifying some of the nucleotide residues of the RNA nucleic acid molecule of the present invention by methylation or the like and a method of converting some of or all of the nucleotide residues into DNA or LNA.

In the formula (I), preferably, some of the nucleotide residues (some of the nucleotide residues in the whole single-stranded nucleic acid) are modified nucleotide residues. Preferably, the modified nucleotide residue is a methylated nucleotide residue, for example. Preferably, the modified site in the nucleotide residue is a ribose site, for example. In the case where the base is a pyrimidine base, for example, the 2'-position and the 4'-position are preferably modified; and in the case where the base is a purine base, for example, the 2'-position and the 4'-position are preferably modified. Further, a method of binding several tens of kDa of polyethylene glycol (PEG) or deoxythymidine to the 5' end and the 3' end may be also employed.

In the formula (I), there is no particular limitation on the number of nucleotide residues in the whole single-stranded nucleic acid, and the number of nucleotide residues is, for example, in the range from 7 to 150, preferably from 10 to 100, and more preferably from 15 to 60.

In the formula (I), there is no particular limitation on the modified nucleotide residue site, and the modified nucleotide residue site is preferably the end of a region capable of forming a stem structure and also the end of a region capable of forming a loop structure. Specific examples thereof include, in the formula (I), the 5' end of $N_2$ (the 3' end of $N_1$), the 3' end of $N_2$ (the 5' end of $N_3$), the 3' end of $N_3$ (the 5' end of $N_4$), the 3' end of $N_4$ (the 5' end of $N_5$), the 3' end of $N_5$ (the 5' end of $N_6$), the 3' end of $N_6$ (the 5' end of $N_7$), and the 3' end of $N_7$ (the 5' end of $N_8$). Among them, the 3' end of $N_3$ (the 5' end of $N_4$), the 3' end of $N_5$ (the 5' end of $N_6$), and the 3' end of $N_2$ (the 5' end of $N_3$) are preferable.

In the formula (I), preferably, some of the nucleotide residues are at least one of LNA and DNA, for example. Especially, in the case where the nucleic acid molecule represented by the formula (I) is an RNA molecule as described above, preferably, some of or all of the nucleotide residues are at least one of LNA and DNA, for example. Further, the RNA molecule may include both LNA and DNA. In the formula (I), there is no particular limitation on the number of LNA nucleotide monomers, and the number of LNA nucleotide monomers is, for example, in the range from 1 to 150, preferably in the range from 1 to 100, and more preferably in the range from 1 to 10. Further, there is no particular limitation on the length of LNA contained in the formula (I), and the length of LNA is, for example, in the range from 1 to 10 residues and preferably 2 residues. In the formula (I), there is no particular limitation on the number of deoxyribonucleotide monomers that form DNA, and the number of deoxyribonucleotide monomers is, for example, in the range from 1 to 150 residues, preferably in the range from 1 to 100 residues, and more preferably in the range from 1 to 30 residues. Further, there is no particular limitation on the length of DNA contained in the formula (I), and the length of DNA is, for example, in the range from 1 to 30 residues, preferably in the range from 3 to 10 residues, and more preferably 4 residues.

Further, in the case where the nucleic acid molecule represented by the formula (I) is an RNA molecule and contains DNA, in the formula (I), DNA is preferably contained in a site capable of forming a stem structure. Specifically, in the formula (I), DNA is preferably contained in some of or all of $N_2$ and $N_7$. Further, in the case where the nucleic acid molecule represented by the formula (I) is an RNA molecule and contains LNA, similarly, in the formula (I), LNA is preferably contained in a site capable of forming a stem structure. Specifically, in the formula (I), LNA is preferably contained in some of or all of $N_2$ and $N_7$.

In the formula (I), preferably, a labeling compound is bound to at least one of the 5' end and the 3' end, for example. More preferably, a labeling compound is bound to the 5' end.

There is no particular limitation on the labeling compound, and examples thereof include biotin, avidin, fluorophore, enzyme, radioisotope, functional groups such as a thiol group and an amino group, an electron acceptor such as methylene blue, an electron donor such as NADPH, organic compounds, inorganic compounds, and an electrochemiluminescent substance such as ruthenium. Among them, biotin is preferable. There is no particular limitation on the fluorophore, and examples thereof include fluorescein and its derivative, rhodamine and its derivative, dansyl chloride and its derivative, and umbelliferone. There is no particular limitation on the enzyme, and examples thereof include horseradish peroxidase, alkaline phosphatase, β-galactosidase, urease, catalase, glucose oxidase, lactic acid dehydrogenase, and amylase. There is no particular limitation on the radioisotope, and examples thereof include iodine ($^{131}$I, $^{125}$I, $^{123}$I, and $^{121}$I), phosphorus ($^{32}$P), sulfur ($^{35}$S), metals (for example, $^{68}$Ga, $^{67}$Ga, $^{68}$Ge, $^{54}$Mn, $^{99}$Mo, $^{99}$Tc, and $^{133}$Xe), and tritium. Examples of labeling compound other than these include luminescent substances such as NADH-, FMNH2-, acridinium ester, and luminol; bioluminescent substances such as luciferase and luciferin; and bio-fluorescent protein such as GFP, although it is not particularly limited.

Preferably, the nucleic acid molecule of the present invention is consisting of at least one sequence selected from the group consisting of the following sequences, for example. In the following sequences, "dN" such as dA, dG, dC, and dT indicate deoxyribonucleotide residues, "N" such as G and C indicate LNA nucleotide residues, and "mN" such as mC and mU indicate methylated ribonucleotide residues.

```
                                                     SEQ ID NO: 1
dAdAdAdAdA-CGCUGAAGAGAAGACGGAAGGAGACGAAGCG-dT

SEQ ID NO: 2
dAdAdAdAdA-GCUGAAGAGAAGACGGAAGGAGACGAAGC-dT

SEQ ID NO: 3
dAdAdAdAdA-dGdCGCUGAAGAGAAGACGGAAGGAGACGAAGCdGdC

SEQ ID NO: 4
dAdAdAdAdA-dGdCdGdCUGAAGAGAAGACGGAAGGAGACGAAdGdCd
GdC

SEQ ID NO: 5
dAdAdAdAdA-GCGCmUGAAGAGAAGACGGAAGGAGACGAAGCGC

SEQ ID NO: 6
dAdAdAdAdA-dGdCdGdCmUGAAGAGAAGACGGAAGGAGACGAAdGdCd
GdC

SEQ ID NO: 7
dAdAdAdAdA-CGCmUGAAGAGAAGACGGAAGGAGACGAAGCG-dT
```

In the nucleic acid molecule of the present invention, preferably, the mouse IgG antibody is at least one of a subtype 1 IgG antibody, a subtype 2a IgG antibody, and a subtype 3 IgG antibody, for example.

In the present invention, there is no particular limitation on the subtype of the mouse-derived IgG antibody, and examples thereof include subtype 1, subtype 2a, subtype 3, and a mixture of IgG antibodies having different subtypes optionally including the subtypes 1, 2a, and 3.

The nucleic acid molecule of the present invention can be produced using nucleic acid molecules such as a so-called RNA pool and IgG antibodies derived from rodents such as mice as target substances according to the method in which a nucleic acid molecule/target substance complex is formed by specifically binding the nucleic acid molecules and the target substances and then the nucleic acid molecules involved in the formation of this complex are exclusively selected. Examples of such methods include the method called Systematic Evolution of Ligands by EXponential enrichment (SELEX method) and the method in which a nucleic acid molecule/target substance complex is obtained using carriers such as agarose gel and polyacrylamide gel and then the nucleic acid molecules involved in the formation of this complex are exclusively selected.

(Production Method of Nucleic Acid Molecule of Present Invention Following SELEX Method)

The nucleic acid molecule of the present invention can be produced according to the SELEX method or a method following this method in which an RNA pool and target substances are allowed to react, the obtained RNA pool-target substance complex is recovered, and then the RNA pool involved in the formation of this complex is exclusively selected from this complex.

RNA pool is a mixture of genes, which is a collective term for gene sequences including a region composed by connecting bases selected from the group consisting of A, G, C, and U and the substitutions of the bases in total of about 20 to 120 (hereinafter, this region is referred to as a "random region"). Accordingly, the RNA pool contains plurality of genes of $4^{20}$ to $4^{120}$ ($10^{12}$ to $10^{72}$) kinds, and preferably contains genes of $4^{30}$ to $4^{60}$ ($10^{18}$ to $10^{36}$) kinds. Examples of the substitutions of bases include appropriately substituted bases such as halogens such as fluorine, chlorine, bromine, and iodine; and alkyl groups such as methyl, ethyl, and propyl.

There is no limitation on the structure of the RNA pool as long as it includes a random region. In the case where the nucleic acid molecule of the present invention is produced following the SELEX method, in the 5' and/or 3' end of the random region, the RNA pool preferably includes a primer region used for the PCR that will be described below and a region recognized by DNA-dependent RNA polymerase. For example, from the 5' end of the random region, the region recognized by DNA-dependent RNA polymerase such as a T7 promoter (hereinafter, this region is referred to as the "RNA polymerase recognition region") is connected to the primer region for DNA-dependent DNA polymerase (hereinafter, this region is referred to as the "5' end-side primer region"), the random region is connected to the 3' end of this 5' end-side primer region, and the primer region of DNA-dependent DNA polymerase (hereinafter, this region is referred to as the "3' end-side primer region") is connected to the 3' end side of this random region. Furthermore, other than these regions, the RNA pool may include a known region which assists the binding to target substances. Moreover, the RNA pool may be the one including the random region, a part of which has a common sequence among the respective RNA pools.

The random region may be prepared by amplifying genes based on the PCR method using, as a template, an initial pool which is made by replacing U in the random region of the RNA pool with T, and then allowing the obtained gene product to react with DNA-dependent RNA polymerase such as T7 polymerase. Furthermore, the random region may be prepared based on the PCR method by synthesizing a gene complementary to an initial pool and allowing a primer consisting of an RNA polymerase recognition region and a sequence complementary to the 5' end-side primer region to anneal to a gene complementary to this primer in the initial pool.

Next, the RNA pool synthesized in this manner and a rodent-derived IgG antibody, which is a target substance, are allowed to bind through an intermolecular force such as hydrogen bonding. An example of the method for this binding includes a method of incubating the RNA pool and the target substance for a fixed period of time in a buffer solution sustaining a function such as binding to the target substance. In this manner, an RNA pool-target substance complex is formed in the buffer solution.

Then, the RNA pool-target substance complex formed in this manner is recovered. The buffer solution contains, besides this complex, the RNA pool and the target substance not involved in the formation of the complex. As a method of recovering the complex, for the purpose of recovering the nucleic acid molecule having a binding affinity to the target substance, a method in which the RNA pool not involved in the formation of the complex in the buffer solution is removed may be employed. Examples of the method include the method of utilizing the difference in the adsorptive property of the target substance and the RNA pool to specific components, and the method of utilizing the difference in the molecular weight of the complex and the RNA pool.

An example of the method of utilizing the difference in the adsorptive property of the target substance and the RNA pool to the specific components includes a method in which, using a membrane capable of adsorbing a target substance such as nitrocellulose, the buffer solution containing the above-described RNA pool-target substance complex is filtered, and then the RNA pool-target substance complex is adsorbed onto this membrane, thereafter, from the remaining RNA pool-target substance complex on the membrane, the RNA pool involved in the formation of the complex is recovered, for example, after releasing the binding between the RNA pool and the target substance in the complex.

Furthermore, an example of the method of utilizing the difference in the molecular weight of the RNA pool-target substance complex and the RNA pool includes the method in which, utilizing a carrier having pores the size of which allows the RNA pool to pass and does not allow the RNA pool-target substance complex to pass, the RNA pool-target substance complex and the RNA pool are separated electrically, and, from this RNA pool-target substance complex, the RNA pool involved in the formation of the complex is recovered.

Next, the gene amplification is performed using the RNA pool involved in the formation of the complex recovered from the thus-obtained RNA pool-target substance complex. An example of the method for this gene amplification includes a method of utilizing the 5' end-side primer region, the 3' end-side primer region, and the RNA polymerase recognition region contained in the RNA pool. The gene amplification of the RNA pool may be performed as follows. For example, using, as a primer, a gene fragment complementary to the 3' end-side primer region of the RNA pool involved in the formation of the complex, cDNA is prepared according to the reverse transcription reaction using RNA-dependent DNA polymerase such as reverse transcriptase originated from avian myeloblastosis virus (AMV Reverse Transcriptase). Then, a PCR reaction using DNA-dependent DNA polymerase is performed utilizing the 5' end-side primer region and the 3' end-side primer region contained in this cDNA, and an in vitro transcription reaction using DNA-dependent RNA polymerase is performed utilizing the RNA polymerase recognition region contained in the thus-obtained gene product.

Using the RNA pool involved in the formation of the complex which is subjected to the gene amplification in this manner and the target substance, the procedures after the process of forming the RNA pool-target substance complex are repeatedly performed, and, in the end, a nucleic acid molecule that specifically binds to IgG antibodies derived from mice and rats serving as target substances can be obtained, i.e., a nucleic acid molecule having a binding affinity to a rodent-derived IgG antibody can be obtained.

(Secondary Structure Prediction in Present Invention)

The nucleic acid molecule of the present invention can be obtained as described above, and a part of the thus-obtained nucleic acid molecule may be modified by reference to the result using the secondary structure prediction method based on the base sequence. There is no particular limitation on the secondary structure prediction method as long as it is the method in which the candidates for the secondary structure of the nucleic acid molecule are searched, and, among the thus-searched candidates for the secondary structure, the energetically stable secondary structure is predicted. An example of the method includes the prediction of the secondary structure based on minimization of the energy function of the candidate for the secondary structure obtained by dividing the base sequence of a nucleic acid molecule into a stem region composing base pairs such as Watson-Crick type and a single-stranded region such as a loop structure composed of bases other than those composing the stem region.

This prediction of the secondary structure based on minimization of the energy function of the candidate for the secondary structure will be described below. First, among the base sequences of the nucleic acid to be analyzed, the candidates for bases composing the base pairs such as Watson-Crick type and the candidates for the single-stranded region other than these candidates for the base pairs were searched. From the all combinations of the searched candidates for the base pairs and the candidates for the single-stranded region, the theoretically impossible combinations such as those having the base composing the base pair candidate overlapping the base composing the single-stranded region candidate are eliminated, and the candidate for the secondary structure is identified. The energy function of the secondary structure candidate is calculated, and the secondary structure which gives minimum calculated energy function is searched among the identified candidates for the secondary structure. In these cases, the calculation method of the energy function of the secondary structure candidate may be a method in which, based on the free energy of each stem region and single-stranded region composing the candidate for the secondary structure, the free energy of the secondary structure candidate is regarded as the energy function of the secondary structure candidate. In this manner, among the identified candidates for the secondary structure, the secondary structure having minimum calculated energy function is regarded as the secondary structure of the base sequence of the nucleic acid molecule to be measured.

The nucleic acid molecule of the present invention may be modified by substitution or deletion of the base composing the characterized part of the secondary structure or by insertion of the base into the characterized part of the secondary structure, by reference to the thus-obtained result of the secondary structure. For example, using the nucleic acid molecule prepared as described above as a parental molecule, some of the bases composing the stem region and/or the single-stranded region of the secondary structure may be substituted. Furthermore, some of the bases composing the stem region and/or the single-stranded region of the secondary structure may be deleted. Moreover, one or more than one bases may be inserted into the stem region and/or the single-stranded region of the secondary structure, to reduce/increase the length of the stem reaction and/or the length of the single-stranded region.

The nucleic acid molecule of the present invention preferably includes, in the secondary structure of the nucleic acid molecule obtained using this secondary structure prediction, a stem region having a stem length of 3 or more at the end of the nucleic acid molecule. Further, in the nucleic acid molecule of the present invention, preferably, the base adjacent to the base at the single-stranded region side end of the stem region having a stem length of 3 or more is a base other than adenine. Furthermore, in the nucleic acid molecule of the present invention, the stem region having a stem length of 3 or more is consisting only of guanine residue(s) and cytosine residue(s). These further enhance the binding affinity to a rodent-derived IgG antibody.

(Use and the Like of Nucleic Acid Molecule of Present Invention)

As described above, the nucleic acid molecule of the present invention has a binding affinity to IgG antibodies derived from rodents such as mice. Accordingly, there is no particular limitation on the use of the nucleic acid molecule of the present invention as long as it utilizes a binding affinity to IgG antibodies derived from rodents such as mice. The nucleic acid molecule of the present invention may be used for detection of a migrating object following the SDS polyacrylamide electrophoresis (SDS-PAGE) method, detection of an object to be measured or a complex containing the object of the enzyme immunoassay (Enzyme-Linked ImmunoSorbent Assay: ELISA), detection of a migrating object following the Northwestern method, or purification of IgG antibodies derived from rodents such as mice or purification of something utilizing IgG antibodies derived from rodents such as mice.

For example, in the case where the nucleic acid molecule of the present invention is used for the SDS-PAGE method, the nucleic acid molecule may be used for detecting migrating proteins or for detecting IgG antibodies derived from rodents such as mice used for detection of migrating proteins.

Further, in the case where the nucleic acid molecule of the present invention is used for the ELISA, the nucleic acid molecule may be used for detecting IgG antibodies derived from rodents such as mice, which are objects to be measured, or detecting IgG antibodies derived from rodents such as mice used for detection of objects to be measured.

Furthermore, in the case where the nucleic acid molecule of the present invention is used for the Northwestern method, the nucleic acid molecule may be used for detecting IgG antibodies derived from rodents such as mice, which are objects to be subjected to electrophoresis, or detecting IgG antibodies derived from rodents such as mice used for detection of a target protein to be subjected to electrophoresis.

Moreover, in the case where the nucleic acid molecule of the present invention is used for purification of IgG antibodies derived from rodents such as mice, the nucleic acid molecule may be utilized in an adequate mode for purifying IgG antibodies derived from rodents such as mice, which are objects to be purified. For example, the nucleic acid molecule of the present invention may be bound to agarose, a bead consisting of a synthetic resin, or the like for use. Examples of the mode in which the nucleic acid molecule is bound to a bead include various modifications such as biotinylation and the like in order to enable it to bind to the carrier used for purification (for example, agarose and a bead consisting of a synthetic resin). Accordingly, the nucleic acid molecule of the present invention may be subjected to various modifications such as biotinylation and the like.

Examples of Application of Nucleic Acid Molecule of Present Invention

Examples of the application of the nucleic acid molecule of the present invention include a reagent containing the obtained nucleic acid molecule and a kit including this reagent, which utilizes a binding affinity to IgG antibodies derived from rodents such as mice. For example, the reagent containing the nucleic acid molecule of the present invention may be used for a detection kit for detecting binding to IgG antibodies derived from rodents such as mice. The objects to be measured using such a kit may be a liquid such as a solution and a suspension or a solid such as cultured cells and tissue sections.

Further, in the detection kit of the present invention, as a reagent other than the nucleic acid molecule of the present invention, substances required for detecting the binding between the target substance and the nucleic acid molecule may be selected appropriately. Such a reagent may be selected suitably according to the nucleic acid molecule used for the detection kit.

For example, the detection using the detection kit of the present invention may be performed following the SDS polyacrylamide electrophoresis (SDS-PAGE) method. In this case, a reagent contained in the detection kit may be a nucleic acid molecule having a binding affinity to IgG antibodies derived from rodents such as mice used for detection of a target protein to be subjected to electrophoresis or a nucleic acid molecule having a binding affinity to IgG antibodies derived from rodents such as mice, which are targets to be subjected to electrophoresis.

Further, the detection using the detection kit of the present invention may be performed following the ELISA. In this case, a reagent contained in the detection kit may be a nucleic acid molecule having a binding affinity to IgG derived from rodents such as mice, which are objects to be measured.

Furthermore, the detection using the detection kit of the present invention may be performed following the Northwestern method. In this case, a reagent contained in the detection kit may be a nucleic acid molecule having a binding affinity to IgG antibodies derived from rodents such as mice used for detection of a protein to be subjected to electrophoresis or a nucleic acid molecule having a binding affinity to IgG antibodies derived from rodents such as mice, which are objects to be subjected to electrophoresis.

The detection method of the present invention includes the following steps:
an immunoprecipitation step of reacting an antibody with an object to be detected in a sample as an antigen to immunoprecipitate;
a separation step of denaturing the immunoprecipitate to separate it from other components in the sample;
a first reaction step of reacting an antibody with the antigen of the immunoprecipitate separated in the separation step; and
a second reaction step of reacting a binder that specifically binds to the antibody in the antibody reaction step, wherein the binder according to the present invention is used as the binder in the second reaction step.

The nucleic acid molecule of the present invention (particularly, RNA molecule) specifically binds to IgG antibodies derived from rodents such as mice. On the other hand, the nucleic acid molecule of the present invention has a low specificity to denatured IgG antibodies derived from rodents such as mice. Therefore, when the nucleic acid molecule of the present invention (particularly, RNA molecule) is used, for example, in the case where detection is performed by the Western blot analysis using mouse IgG after SDS-PAGE, since the nucleic acid molecule of the present invention is unlikely to bind to antibodies denatured by SDS, an object to be detected can be detected clearly while suppressing noise. Accordingly, in the detection method of the present invention, preferably, SDS-PAGE is employed for the separation step and the Western blot analysis is employed for the first reaction step and the second reaction step.

Next, Examples of the present invention will be described. However, the present invention is not limited by the following Examples.

EXAMPLE

The following Table 1 shows clones of the aptamers for a mouse IgG antibody (hereinafter, referred to as the "mouse IgG aptamer") used in the following Examples. "Modification" in Table 1 indicates the modification of each sequence. Specifically, "5'-biotin" indicates that biotin is bound to the 5' end; "dA 5 mer" indicates 5 mer polydeoxynucleotide residue; "stem LNA-2 bp" indicates that the sequence includes 2 bp LNA in a region capable of forming a stem structure and "stem LNA-4 bp" indicates that the sequence includes 4 bp LNA in a region capable of forming a stem structure; "stem DNA-2 bp" indicates that the sequence includes 2 bp DNA in a region capable of forming a stem structure and "stem DNA-4 bp" indicates that the sequence includes 4 bp DNA in a region capable of forming a stem structure; "+dT" indicates that the sequence includes a deoxythymidine residue at the 3' end; and "methylation 21C", "methylation 31C", and "methylation 10U" respectively indicate that the $21^{st}$ C, the $31^{st}$ C, and the $10^{th}$ U are methylated. Further, in "Sequence" in Table 1, "dN" indicates deoxyribonucleotide, "underlined N" indicates LNA nucleotide monomer, and "mN" indicates methylation of the 2'-position of the base (2'-O-methyl). FIGS. 1 to 3 show the predicted secondary structures with respect to these aptamers.

TABLE 1

| Clone Name | SEQ ID NO | Modification | Sequence |
|---|---|---|---|
| MIG-m040 | 5 | 5'-biotin dA 5mer methylation 10U | biotin-dAdAdAdAdA-GCGCmUGAAGAGAAGACGGAAGGAGACGAAGCGC |
| MIG-m034 | 1 | 5'-biotin dA 5mer stem LNA- | biotin-dAdAdAdAdA-CGCUGAAGAGAAGACGGAAGGAGACGAAG<u>CG</u>-dT |

TABLE 1-continued

| Clone Name | SEQ ID NO | Modification | Sequence |
|---|---|---|---|
| | | 2bp + dT | |
| MIG-m035 | 2 | 5'-biotin dA 5mer stem LNA-2bp + dT | biotin-dAdAdAdAdA-<br>GCUGAAGAGAAGACGGAAGGAGACGAAGC-dT |
| MIG-m036 | 3 | 5'-biotin dA 5mer stem DNA-2bp | biotin-dAdAdAdAdA-<br>dGdCGCUGAAGAGAAGACGGAAGGAGACGAAGC dGdC |
| MIG-m037 | 4 | 5'-biotin dA 5mer stem DNA 4bp | biotin-dAdAdAdAdA-<br>dGdCdGdCUGAAGAGAAGACGGAAGGAGACGAA dGdCdGdC |
| MIG-m041 | 6 | 5'-biotin dA 5mer methylation 10U stem DNA-4bp | biotin-dAdAdAdAdA-<br>dGdCdGdCmUGAAGAGAAGACGGAAGGAGACGAA dGdCdGdC |
| MIG-m042 | 7 | 5'-biotin dA 5mer methylation 9U stem LNA-2bp + dT | biotin-dAdAdAdAdA-<br>CGCmUGAAGAGAAGACGGAAGGAGACGAAGCG-dT |

Example 1

First, with respect to the mouse IgG aptamer, the binding affinity to a mouse-derived IgG antibody was evaluated by the Northwestern blot analysis. MIG-m034, MIG-m041, and MIG-m042 summarized in Table 1 were used as aptamers. MIG-m041 is the aptamer in which the $10^{th}$ uracil residue is methylated and 4 bp DNA is contained in a region capable of forming a stem structure. MIG-m042 is the aptamer in which the $9^{th}$ uracil residue is methylated and 2 bp LNA is contained in a region capable of forming a stem structure.

The Northwestern blot analysis was performed as follows. First, 50 ng, 100 ng, and 200 ng of FLAG-BAP Control Protein (SIGMA #P7582) used as antigens were transcribed to a PVDF membrane after SDS-PAGE. Then, ANTI-FLAG M2 Monoclonal Antibody (SIGMA #F3165 Lot #086K6012), which was diluted to 1/1000, used as a primary antibody was allowed to bind to the antigens on the PVDF membrane, and each of the aptamers was allowed to bind to the primary antibody. Thereafter, peroxidase labeled streptavidin (produced by GE Healthcare) and CPS-1 substrate (produced by SIGMA) were added, and the substrate was allowed to emit light, and thereby performed photosensitization to a film. Here, the aptamer concentration of MIG-m034 was 20 nM and the aptamer concentration of each of MIG-m041 and MIG-m042 was 10 nM.

Figure 4:
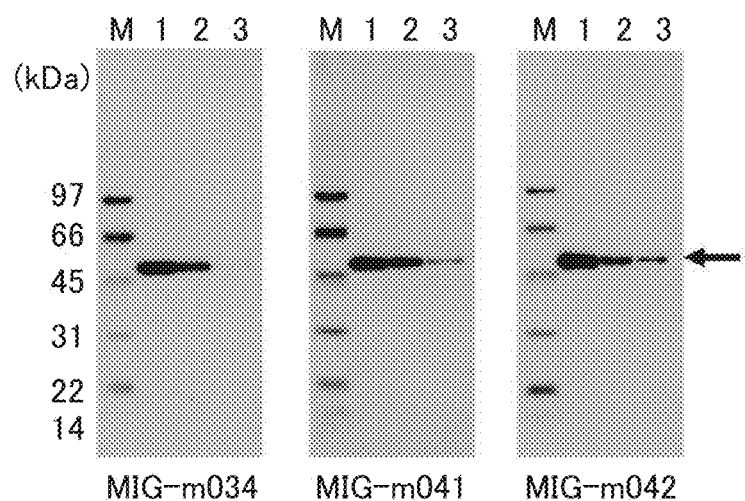
FIGS. 4A to 4C are photographs showing the results of the Northwestern blot analysis.

The results thereof are shown in FIGS. 4A to 4C. FIGS. 4A to 4C are photographs showing the results of the Northwestern blot analysis. FIG. 4A shows the result for MIG-m034, FIG. 4B shows the result for MIG-m041, and FIG. 4C shows the result for MIG-m042. In each of FIGS. 4A to 4C, the lane M shows a biotinylated molecular weight marker, the lane 1 shows the result obtained using 200 ng of FLAG-BAP, the lane 2 shows the result obtained using 100 ng of FLAG-BAP, and the lane 3 shows the result obtained using 50 ng of FLAG-BAP. As shown in FIGS. 4A to 4C, with respect to all the aptamers, the signal specific to the antigen can be detected. Among them, the signal was sufficiently seen with MIG-m041 and MIG-m042 although the aptamer concentration of each of them was 10 nM, which is low.

Example 2

The binding between the mouse IgG aptamers and the mouse-derived IgG antibodies of various subtypes was analyzed. MIG-m034, MIG-m041, and MIG-m042 summarized in Table 1 were used as aptamers.

The analysis of binding was performed using BIACORE 3000 (produced by GE Healthcare) according to its instruction manual. Further, from the signal intensity (RU: Resonance Unit) measured using the BIACORE, the analysis was performed with 1:1 Langmuir binding model using BIAevaluation software, and the dissociation constant between each of the aptamers and each of the mouse IgG antibodies was obtained. The conditions, method, and the like of the measurement using the BIACORE were according to the following documents.

(Documents)
Yoshihito Yoshida*, Nobuya Sakai*, Hiromi Masuda, Makio Furuichi, Fumiko Nishikawa, Satoshi Nishikawa, Hiroshi Mizuno and Iwao Waga:
"Rabbit antibody detection with RNA aptamers"
Analytical Biochemistry, Vol. 375, pp. 217-222, (2008)

Figure 5:
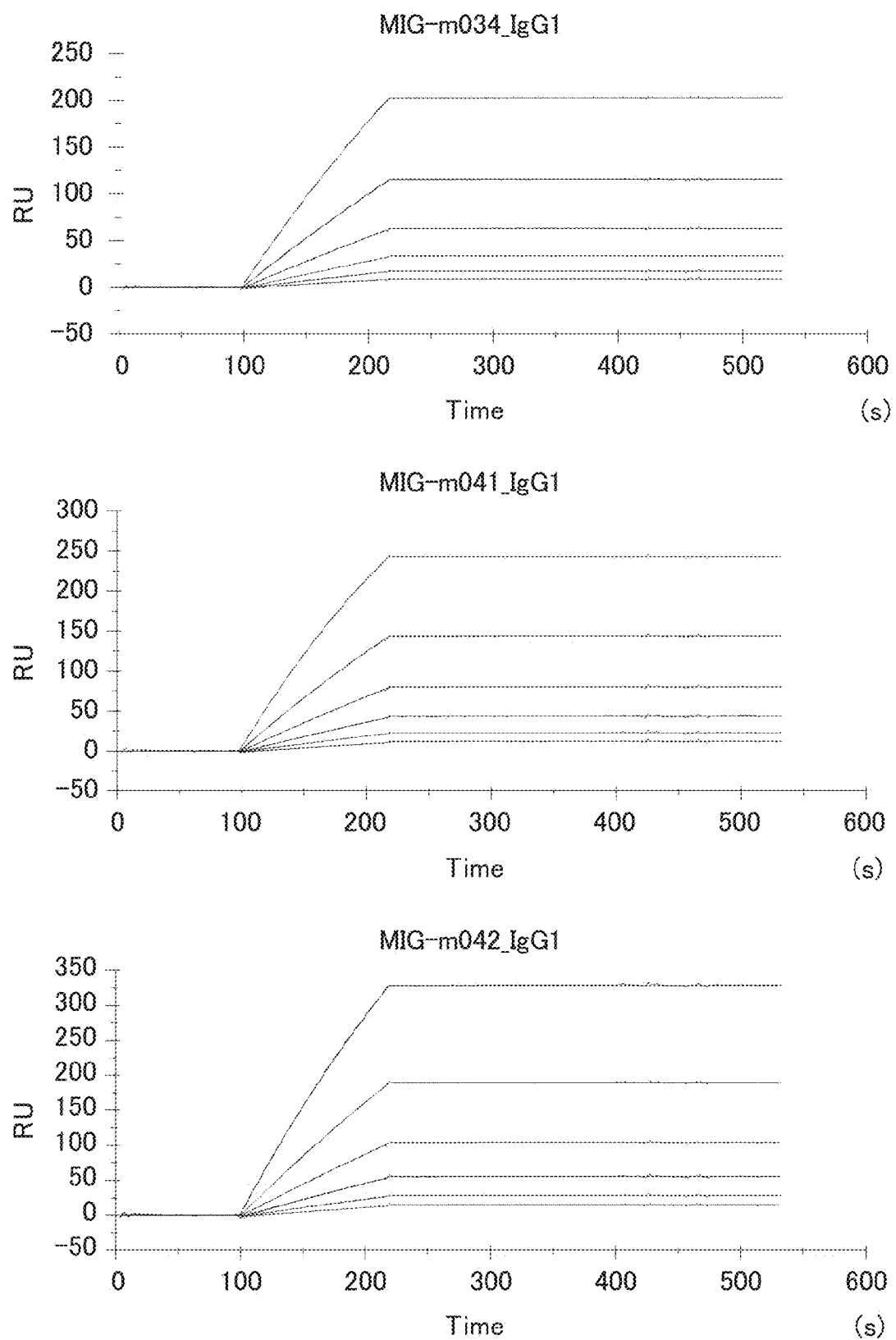
FIG. 5 shows graphs showing the analysis results by BIACORE.
Figure 6:
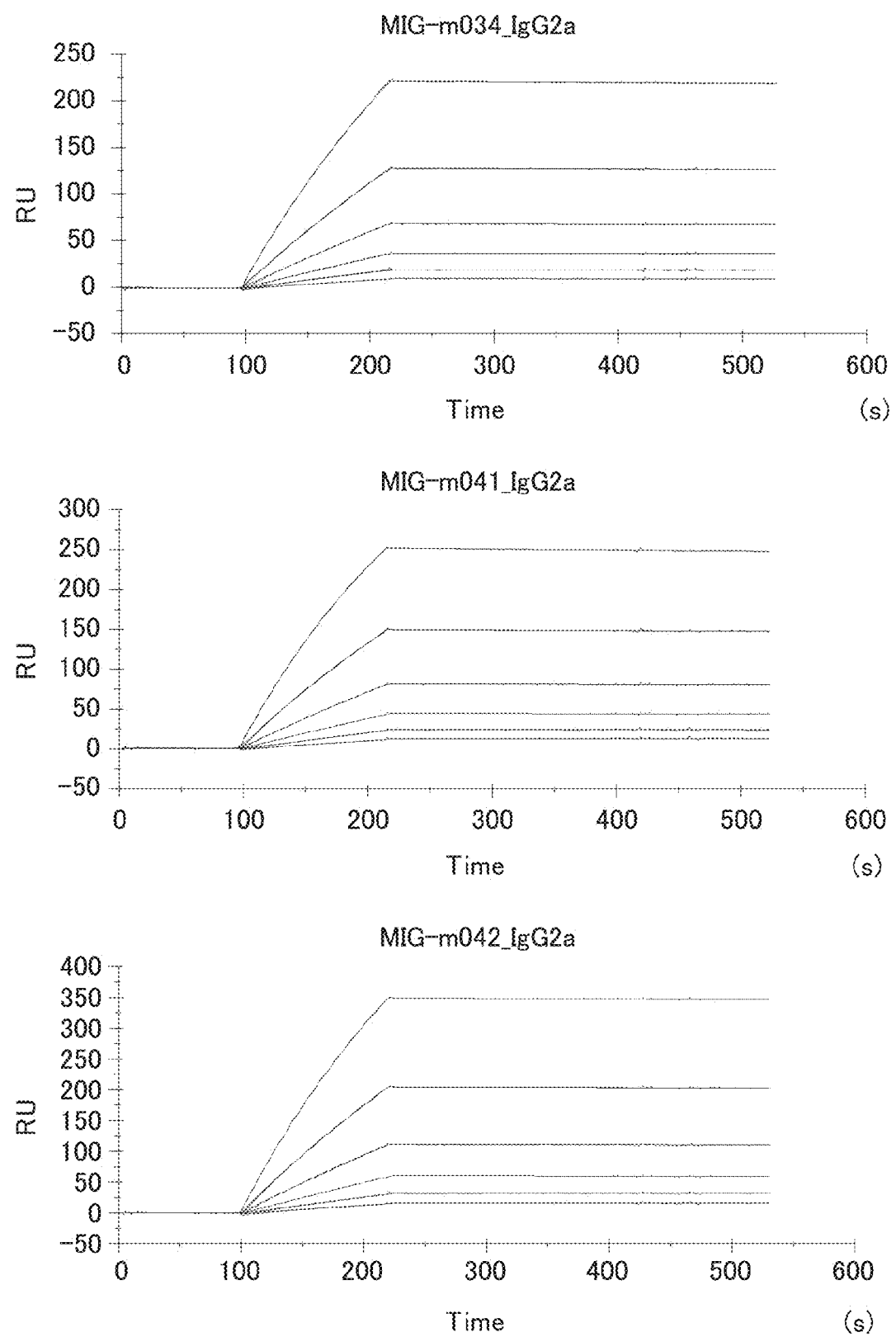
FIG. 6 shows graphs showing the analysis results by BIACORE.
Figure 7:
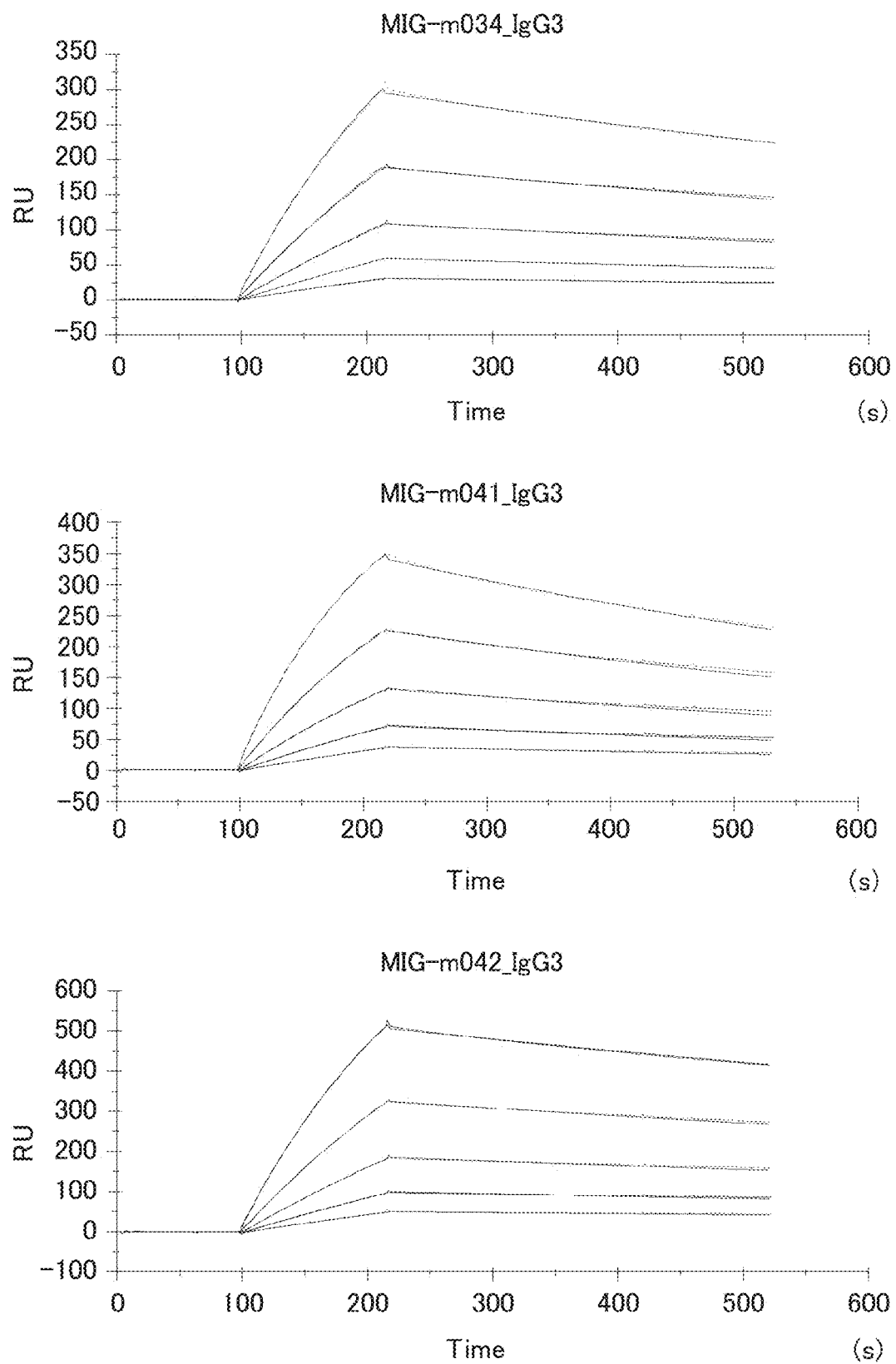
FIG. 7 shows graphs showing the analysis results by BIACORE.

The results thereof are shown in FIGS. 5 to 7. FIGS. 5 to 7 are graphs showing the change in the signal intensity over time. FIG. 5 shows the binding between the subtype 1 mouse IgG antibody and the aptamers, FIG. 6 shows the binding between the subtype 2a mouse IgG and the aptamers, and FIG. 7 shows the subtype 3 mouse IgG and the aptamers. Each of FIGS. 5 to 7 shows the result for MIG-m034, the result for MIG-m041, and the result for MIG-m042 in this order from the top. Further, in each of the graphs, the vertical axis indicates the signal intensity (RU) measured using the BIACORE and the horizontal axis indicates the analysis time (sec). In the horizontal axis, "100 seconds" is the time when the injection of a target to be analyzed to a flow cell at the flow rate of 20 μL/min is started. The injection was maintained for 2 minutes (120 seconds), and then a running buffer was sent for 3 minutes (180 seconds) to obtain the sensorgrams showing the interaction between the aptamers and IgG. The global fitting analysis was performed and the sensorgrams were obtained under different target concentration conditions for obtaining correct Kd values. The six results show the sensorgrams having analyte concentrations of 100 nM, 50 nM, 25 nM, 12.5 nM, 6.25 nM, and 0 nM in decreasing order of the signal intensity.

The following Table 2 shows the dissociation constant between each of the mouse IgG aptamers and each of the mouse IgG antibody-subtypes.

TABLE 2

| Clone Name | SEQ ID NO | Kd (M) | | |
|---|---|---|---|---|
| | | IgG1 | IgG2a | IgG3 |
| MIG-m034 | 1 | 1E−12 or less | 9.95E−10 | 8.80E−09 |
| MIG-m041 | 6 | 1E−12 or less | 9.59E−10 | 8.40E−09 |
| MIG-m042 | 7 | 1E−12 or less | 4.36E−10 | 5.57E−09 |

The results summarized in FIGS. 5 to 7 and Table 2 tell that all the aptamers show a good binding affinity to each of the mouse IgG antibody-subtypes. Among them, it was found that MIG-m041 and MIG-m042, which are obtained by modifying MIG-m034, each have a higher binding affinity to each of the mouse IgG antibody-subtypes and have a very specific binding affinity especially to IgG1. The binding force of MIG-m041, which is obtained by substituting a stem region with DNA based on MIG-m034 in which a G-C pair in a stem is LAN, is substantially equal to that of MIG-m042, which is obtained by methylating the 9-position uridine of MIG-m034. It is considered that the base pair in the stem region and U adjacent thereto are not involved in the binding of mouse IgG.

Example 3

Figure 8:
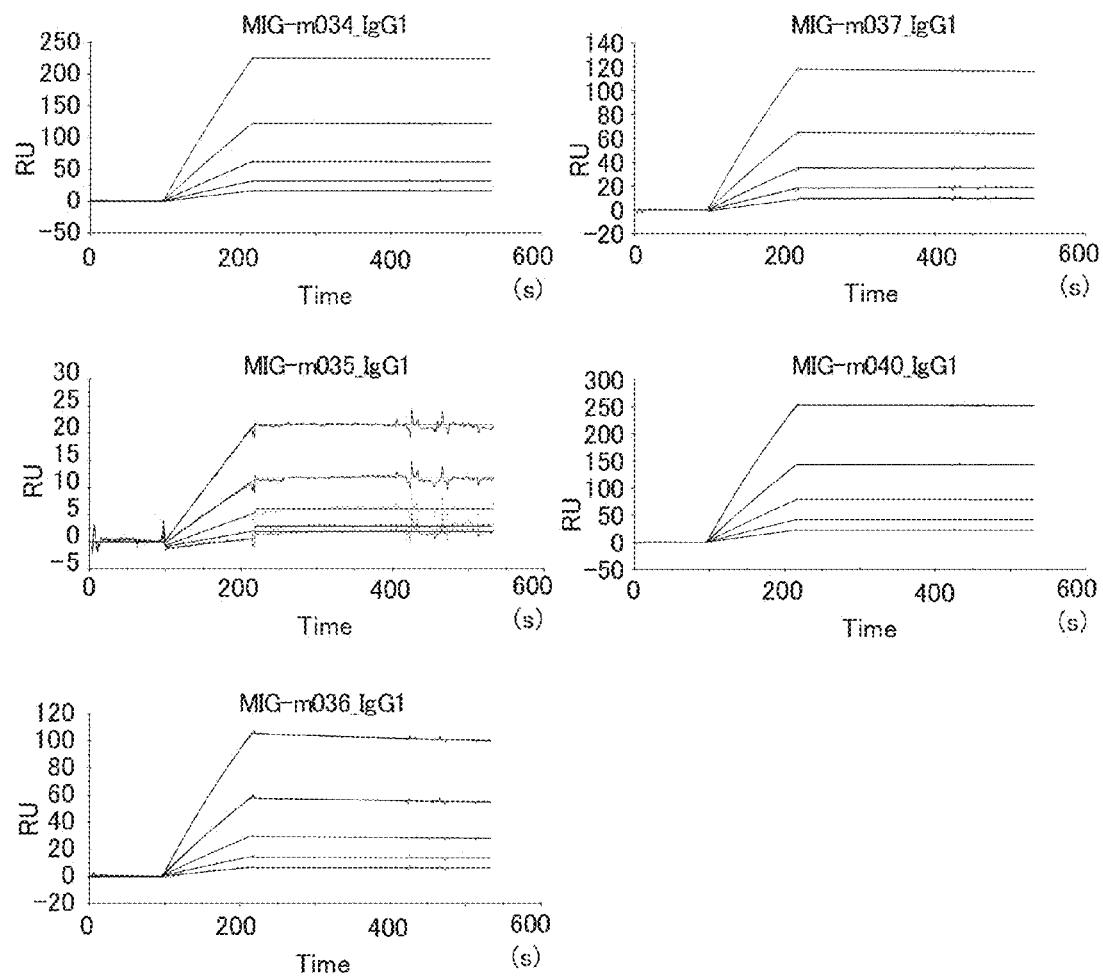
FIG. 8 shows graphs showing the analysis results by BIACORE.
Figure 9:
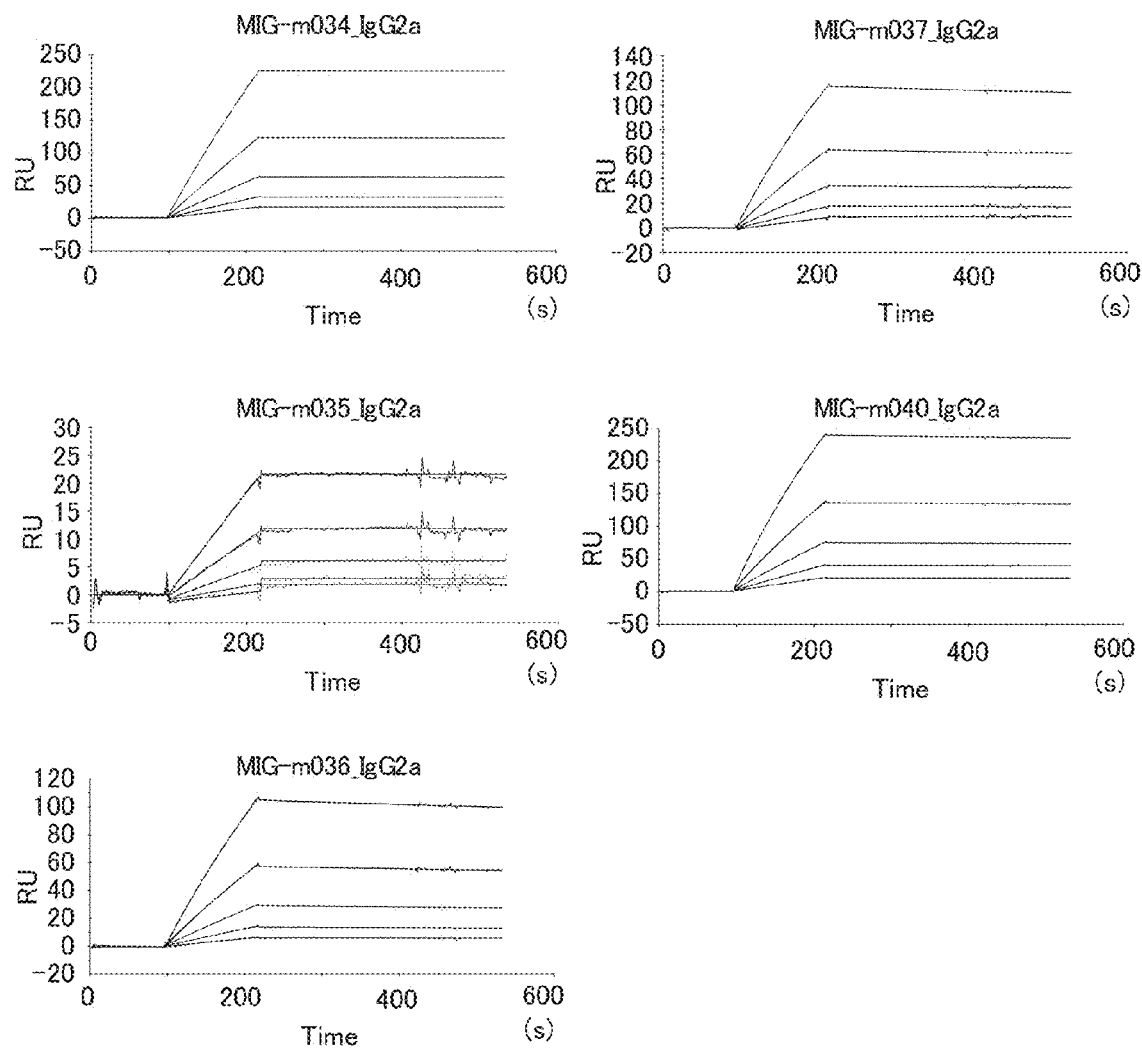
FIG. 9 shows graphs showing the analysis results by BIACORE.
Figure 10:
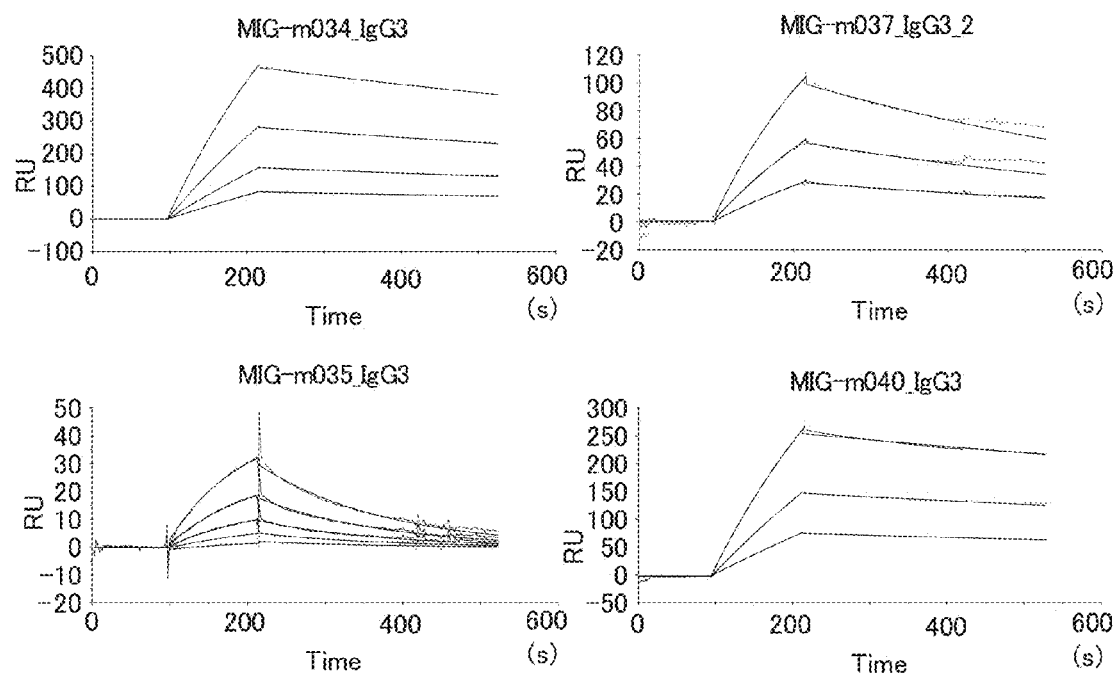
FIG. 10 shows graphs showing the analysis results by BIACORE.

The experiment was performed in the same manner as in Example 2 except that MIG-m034, MIG-m035, MIG-m036, MIG-m037, and MIG-m040 were used as aptamers. The results thereof are shown in FIGS. 8 to 10. FIGS. 8 to 10 are graphs showing the change in the signal intensity over time and respectively show the result obtained using the subtype 1 mouse IgG, the result obtained using the subtype 2a mouse IgG, and the result obtained using the subtype 3 mouse IgG. Further, the following Table 3 shows the dissociation constant between each of the aptamers and each of the mouse IgG-subtypes obtained from the measurement result using the BIACORE. The results summarized in Table 3 tell that these aptamers each have high general versatility as a secondary antibody reagent and are good in the binding force. Further, since it was considered that the base pair in the stem region and U adjacent thereto are not involved in the binding of mouse IgG from Example 1, a clone having a systematic modified base was produced to obtain the Kd value. Since all the clones have substantially the same binding force to each of the mouse antibody subtypes, it was considered that the stem region was not involved in the binding with respect to all the subtypes and also that all the aptamers have the same binding mode to each of the subtypes.

TABLE 3

| Clone Name | SEQ ID NO | Kd (M) | | |
|---|---|---|---|---|
| | | IgG1 | IgG2a | IgG3 |
| MIG-m034 | 1 | 6.34E−10 | 1.09E−09 | 8.33E−09 |
| MIG-m035 | 2 | 1E−12 or less | 1.92E−09 | 1.39E−07 |

TABLE 3-continued

| Clone Name | SEQ ID NO | Kd (M) | | |
|---|---|---|---|---|
| | | IgG1 | IgG2a | IgG3 |
| MIG-m036 | 3 | 5.48E−09 | 4.61E−09 | 1.38E−08 |
| MIG-m037 | 4 | 1.70E−09 | 3.70E−09 | 9.85E−09 |
| MIG-m040 | 5 | 4.11E−10 | 1.23E−09 | 3.46E−09 |

Example 4

Each of the aptamers was added to an FBS solution, and the sample was maintained at room temperature (20° C.) for 30 minutes, 1 hour, 2 hours, and 4 hours after addition. The equal amount of 2×Urea sample solution in which an RNase inhibitor (RNAsecure, produced by Ambion) was added was added to each of the samples of after maintenance, and the resultant was treated at 60° C. for 10 minutes and the reaction of nuclease was stopped. 10 to 20 ng of the sampled RNA was added to 15% 7M urea polyacrylamide gel (1×TBE, 140 mm×70 mm×1 mm gel plate) per lane, electrophoresis was performed at a constant voltage of 200 V for 80 to 90 minutes, and then the gel was stained with SYBR Gold (produced by Invitrogen Corporation) and photographed on a UV transilluminator. Among the image data obtained, the band of the full-length of the aptamer was quantified by performing the densitometry analysis using ImageJ 1.37v (Abramoff, M. D., Magelhaes, P. J., Ram, S. J. "Image Processing with ImageJ" Biophotonics International, 11,7,36-42,2004.), and the stability of each aptamer was evaluated. In each of the samples, the final concentration of the aptamer was 10 µM and the final concentration of the FBS was 1%. MIG-m034, MIG-m041, and MIG-m042 were used as aptamers.

Figure 11:
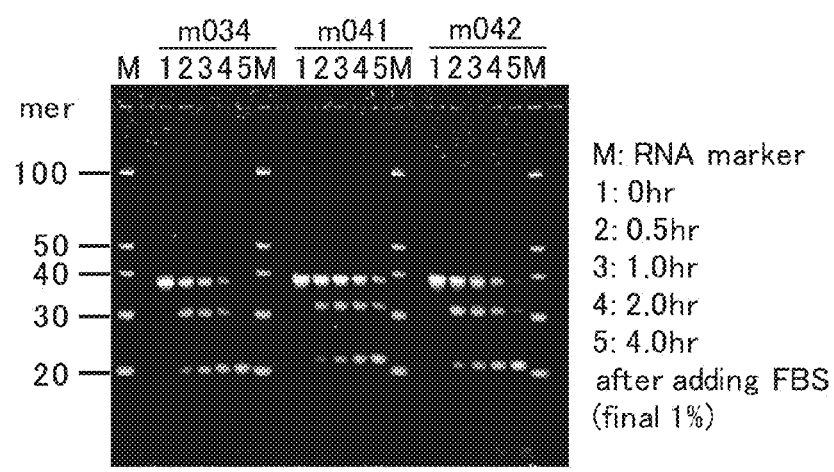
FIG. 11 is an electrophoresis photograph showing the analysis results of the stability of the aptamers.

The results thereof are shown in FIG. 11. FIG. 11 is an electrophoresis photograph showing the aptamer samples of after maintenance for fixed periods of time. In FIG. 11, each of m034, m041, and m042 indicates the kind of the aptamer. Further, the lane M shows an RNA marker, and the lanes 1 to 5 respectively indicate the results of the maintenance time of 0 hour, 0.5 hours, 1.0 hour, 2.0 hours, and 4.0 hours. With respect to the maintenance time, "0 hour" was the additional timing of the aptamer to the FBS solution.

Figure 12:
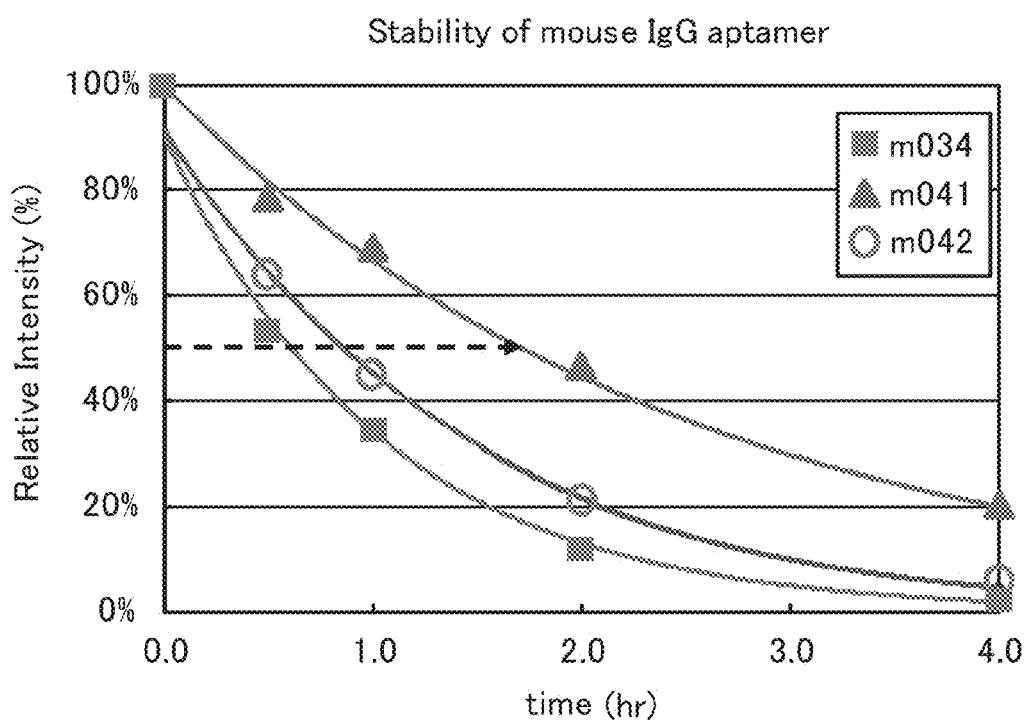
FIG. 12 is a graph showing the analysis results of the stability of the aptamers.

FIG. 12 shows the quantified result of the analysis of the electrophoresis. FIG. 12 is a graph showing the change in the band intensity over time in the electrophoresis.

The vertical axis indicates the relative intensity (%) and the horizontal axis indicates the maintenance time (hr). As shown in FIG. 12, the calculated half-life of the aptamer in FBS, which was diluted to 1/100, was 1 to 2 hours. From the result above, it was found that the half-life of the aptamer can be extended by modifying the aptamer at a site not involved in binding with IgG.

Example 5

First, with respect to the MIG-m041 aptamer, the binding affinity to a mouse-derived IgG antibody was evaluated by the Northwestern blot analysis. Conditions for the experiment were as follows. The experiment was performed in the same manner as in Example 1 except that anti-FLAG mouse IgG (0.5 µg), the combination of anti-FLAG mouse IgG (0.5 µg) and FLAG-BAP protein (100 ng), and FLAG-BAP protein (100 ng) were used as antigens and 20 nM MIG-m041 was used as an aptamer.

Comparative Example 1

As the Comparative Example of Example 5, the Western blot analysis was performed with respect to the aforementioned antigens. The blotting was performed in the same manner as in Example 5 except that a biotinylated-anti-mouse IgG goat antibody (produced by CHEMICON, AP124B) was used in place of the MIG-m041 aptamer.

Figures 13A, 13B:
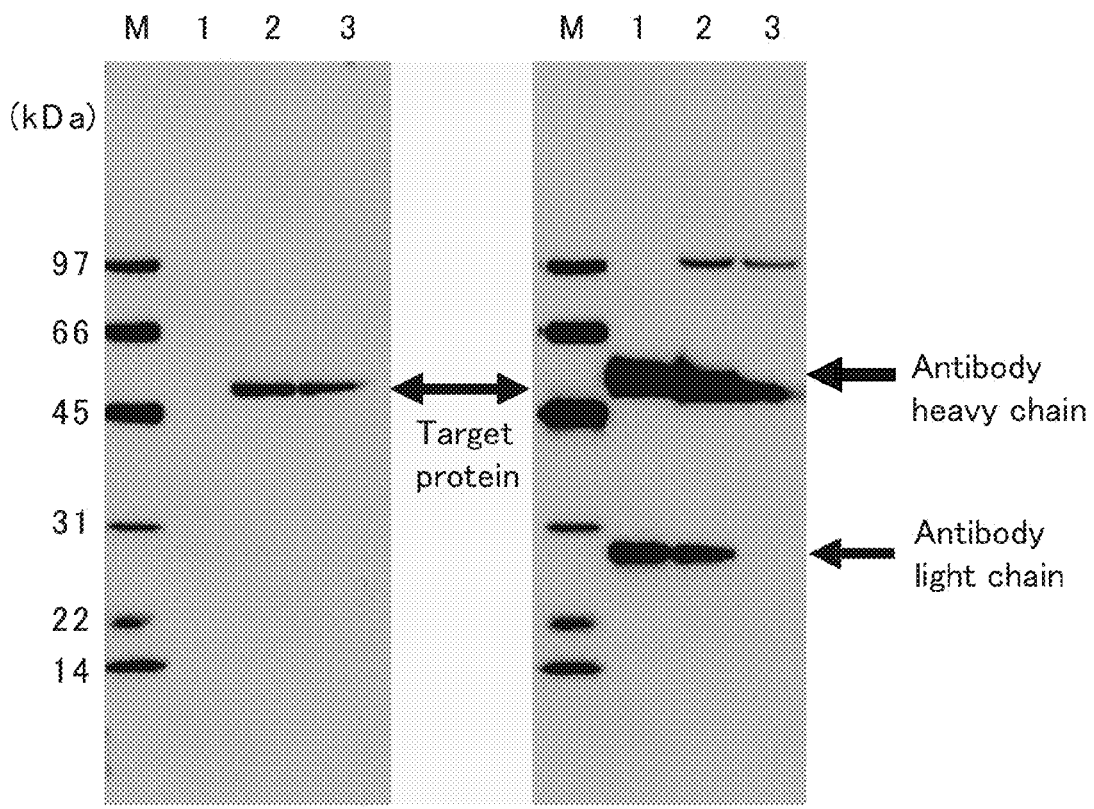
FIGS. 13A and 13B are electrophoresis photographs each showing the analysis results of the binding specificity between the aptamer and the mouse-derived IgG antibodies.

The results of Example 5 and Comparative Example 1 are shown in FIGS. 13A and 13B. FIG. 13A is a photograph showing the results of the Northwestern blot analysis of Example 5, and FIG. 13B is a photograph showing the results of the Western blot analysis of Comparative Example 1. In FIGS. 13A and 13B, the lane M shows a biotinylated molecular weight marker, the lane 1 shows the result obtained using anti-FLAG mouse IgG (0.5 µg), the lane 2 shows the result obtained using anti-FLAG mouse IgG (0.5 µg) and FLAG-BAP protein (100 ng), and the lane 3 shows the result obtained using FLAG-BAP protein (100 ng). As shown in FIG. 13A, in the case where the MIG-m041 aptamer was used, only the signal of the FLAG-BAP protein, which is a target protein, was detected. On the other hand, as shown in FIG. 13B, in the case of the Western blot analysis using an ordinary secondary antibody, the signals of the antibody heavy chain and antibody light chain generated by denaturation of the anti-FLAG mouse IgG were detected. From these results, it became evident that this aptamer binds only to native IgG but not binds to denatured IgG. Further, it was found that when this aptamer is used for the blotting of the sample after immunoprecipitation, a clear result without the background of the antibody heavy chain and the antibody light chain can be obtained.

The present invention was described above with reference to the preferred embodiments of the present invention. Although the present invention was described with reference to specific examples, it is obvious that various modification and changes can be made in the specific examples without departing from wide-range objects and the scope of the present inventioned defined in Claims. In other words, it shall not be interpreted that the present invention is limited by the details of the specific examples and the attached drawings.

INDUSTRIAL APPLICABILITY

The nucleic acid molecule of the present invention can be applied to any field in which a rodent-derived IgG antibody is used. For example, the nucleic acid molecule of the present invention can be applied to a wide range of fields such as a laboratory test and a biochemical test.

The invention claimed is:

1. An isolated single-stranded nucleic acid molecule having a specific binding affinity to a mouse-derived IgG antibody, wherein said isolated single-stranded nucleic acid molecule comprises a nucleotide sequence selected from the group consisting of SEQ ID NOs: 1-7.

2. The isolated single-stranded nucleic acid molecule according to claim 1, wherein the mouse-derived IgG antibody is at least one of a subtype 1 IgG antibody, a subtype 2a IgG antibody, and a subtype 3 IgG antibody.

3. A binder for a mouse-derived IgG antibody, comprising the isolated single-stranded nucleic acid molecule according to claim 1.

4. A detection reagent for detecting a mouse-derived IgG antibody, comprising the binder according to claim 3.

5. A detection kit for detecting a mouse-derived IgG antibody, comprising the detection reagent according to claim 4.

6. A detection method comprising the following steps:
an immunoprecipitation step of reacting an antibody with an object to be detected in a sample as an antigen to immunoprecipitate;
a separation step of denaturing the immunoprecipitate to separate it from other components in the sample;
a first reaction step of reacting an antibody with the antigen of the immunoprecipitate separated in the separation step; and
a second reaction step of reacting a binder that specifically binds to the antibody in the first reaction step,
wherein the binder according to claim 3 is used as the binder in the second reaction step.

7. The detection method according to claim 6, wherein SDS-PAGE is employed for the separation step and a Western blot analysis is employed for the first reaction step and the second reaction step.

8. The isolated single-stranded nucleic acid molecule according to claim 1, wherein said isolated single-stranded nucleic acid molecule comprises the nucleotide sequence of SEQ ID NO: 1.

9. The isolated single-stranded nucleic acid molecule according to claim 1, wherein said isolated single-stranded nucleic acid molecule comprises the nucleotide sequence of SEQ ID NO: 2.

10. The isolated single-stranded nucleic acid molecule according to claim 1, wherein said isolated single-stranded nucleic acid molecule comprises the nucleotide sequence of SEQ ID NO: 3.

11. The isolated single-stranded nucleic acid molecule according to claim 1, wherein said isolated single-stranded nucleic acid molecule comprises the nucleotide sequence of SEQ ID NO: 4.

12. The isolated single-stranded nucleic acid molecule according to claim 1, wherein said isolated single-stranded nucleic acid molecule comprises the nucleotide sequence of SEQ ID NO: 5.

13. The isolated single-stranded nucleic acid molecule according to claim 1, wherein said isolated single-stranded nucleic acid molecule comprises the nucleotide sequence of SEQ ID NO: 6.

14. The isolated single-stranded nucleic acid molecule according to claim 1, wherein said isolated single-stranded nucleic acid molecule comprises the nucleotide sequence of SEQ ID NO: 7.

* * * * *

SEQUENCE LISTING

```
<160> NUMBER OF SEQ ID NOS: 7

<210> SEQ ID NO 1
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: residue 1 is biotinylated.
<220> FEATURE:
<221> NAME/KEY: misc_feature
<222> LOCATION: (37)..(37)
<223> OTHER INFORMATION: residue 37 is a deoxythymine residue.
<220> FEATURE:
<221> NAME/KEY: misc_feature
<222> LOCATION: (35)..(36)
<223> OTHER INFORMATION: residues 35 and 36 are LNA residues.
<220> FEATURE:
<221> NAME/KEY: misc_feature
<222> LOCATION: (6)..(7)
<223> OTHER INFORMATION: residues 6 and 7 are LNA residues.
<220> FEATURE:
<221> NAME/KEY: misc_feature
<222> LOCATION: (1)..(5)
<223> OTHER INFORMATION: residues 1 to 5 are deoxyadenine residues.

<400> SEQUENCE: 1
aaaaacgcug aagagaagac ggaaggagac gaagcgt                              37

<210> SEQ ID NO 2
<211> LENGTH: 35
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: residue 1 is biotinylated.
<220> FEATURE:
<221> NAME/KEY: misc_feature
<222> LOCATION: (1)..(5)
<223> OTHER INFORMATION: residues 1 to 5 are deoxyadenine residues.
<220> FEATURE:
<221> NAME/KEY: misc_feature
```

-continued

```
<222> LOCATION: (35)..(35)
<223> OTHER INFORMATION: residue 35 is a deoxythymine residue.
<220> FEATURE:
<221> NAME/KEY: misc_feature
<222> LOCATION: (6)..(7)
<223> OTHER INFORMATION: residues 6 and 7 are LNA residues.
<220> FEATURE:
<221> NAME/KEY: misc_feature
<222> LOCATION: (33)..(34)
<223> OTHER INFORMATION: residues 33 and 34 are LNA residues.

<400> SEQUENCE: 2
aaaaagcuga agagaagacg gaaggagacg aagct                              35

<210> SEQ ID NO 3
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(7)
<223> OTHER INFORMATION: residues 1 to 7 are deoxyribonucleotide
      residues.
<220> FEATURE:
<221> NAME/KEY: misc_feature
<222> LOCATION: (1)..(1)
<223> OTHER INFORMATION: residue 1 is biotinylated.
<220> FEATURE:
<221> NAME/KEY: misc_feature
<222> LOCATION: (37)..(38)
<223> OTHER INFORMATION: residues 37 and 38 are deoxyribonucleotide
      residues.

<400> SEQUENCE: 3
aaaaagcgcu gaagagaaga cggaaggaga cgaagcgc                           38

<210> SEQ ID NO 4
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(9)
<223> OTHER INFORMATION: residues 1 to 9 are deoxyribonucleotide
      residues.
<220> FEATURE:
<221> NAME/KEY: misc_feature
<222> LOCATION: (1)..(1)
<223> OTHER INFORMATION: residue 1 is biotinylated.
<220> FEATURE:
<221> NAME/KEY: misc_feature
<222> LOCATION: (35)..(38)
<223> OTHER INFORMATION: residues 35 to 38 are deoxyribonucleotide
      residues.

<400> SEQUENCE: 4
aaaaagcgcu gaagagaaga cggaaggaga cgaagcgc                           38

<210> SEQ ID NO 5
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: residues 1 to 5 are deoxyadenine residues.
<220> FEATURE:
```

```
<221> NAME/KEY: misc_feature
<222> LOCATION: (10)..(10)
<223> OTHER INFORMATION: residue 10 is methylated.
<220> FEATURE:
<221> NAME/KEY: misc_feature
<222> LOCATION: (1)..(1)
<223> OTHER INFORMATION: residue 1 is biotinylated.

<400> SEQUENCE: 5
aaaaagcgcu gaagagaaga cggaaggaga cgaagcgc                                    38

<210> SEQ ID NO 6
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(9)
<223> OTHER INFORMATION: residues 1 to 9 are deoxyribonucleotide
      residues.
<220> FEATURE:
<221> NAME/KEY: misc_feature
<222> LOCATION: (35)..(38)
<223> OTHER INFORMATION: residues 35 to 38 are deoxyribonucleotide
      residues.
<220> FEATURE:
<221> NAME/KEY: misc_feature
<222> LOCATION: (10)..(10)
<223> OTHER INFORMATION: residue 10 is methylated.
<220> FEATURE:
<221> NAME/KEY: misc_feature
<222> LOCATION: (1)..(1)
<223> OTHER INFORMATION: residue 1 is biotinylated.

<400> SEQUENCE: 6
aaaaagcgcu gaagagaaga cggaaggaga cgaagcgc                                    38

<210> SEQ ID NO 7
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: residue 1 is biotinylated.
<220> FEATURE:
<221> NAME/KEY: misc_feature
<222> LOCATION: (37)..(37)
<223> OTHER INFORMATION: residue 37 is a deoxythymine residue.
<220> FEATURE:
<221> NAME/KEY: misc_feature
<222> LOCATION: (35)..(36)
<223> OTHER INFORMATION: residues 35 and 36 are LNA residues.
<220> FEATURE:
<221> NAME/KEY: misc_feature
<222> LOCATION: (6)..(7)
<223> OTHER INFORMATION: residues 6 and 7 are LNA residues.
<220> FEATURE:
<221> NAME/KEY: misc_feature
<222> LOCATION: (9)..(9)
<223> OTHER INFORMATION: residue 9 is methylated.
<220> FEATURE:
<221> NAME/KEY: misc_feature
<222> LOCATION: (1)..(5)
<223> OTHER INFORMATION: residues 1 to 5 are deoxyadenine residues.

<400> SEQUENCE: 7
aaaaacgcug aagagaagac ggaaggagac gaagcgt                                     37
```